(12) United States Patent
Stad et al.

(10) Patent No.: US 8,979,857 B2
(45) Date of Patent: Mar. 17, 2015

(54) MODULAR MEDICAL TOOL AND CONNECTOR

(75) Inventors: Shawn D. Stad, Fall River, MA (US); Mark Gracia, Rochester, MA (US)

(73) Assignee: DePuy Synthes Products, LLC, Raynham, MA (US)

( * ) Notice: Subject to any disclaimer, the term of this patent is extended or adjusted under 35 U.S.C. 154(b) by 1161 days.

(21) Appl. No.: 10/959,598

(22) Filed: Oct. 6, 2004

(65) Prior Publication Data
US 2006/0074432 A1 Apr. 6, 2006

(51) Int. Cl.
*A61B 17/58* (2006.01)
*A61F 2/46* (2006.01)
*A61B 17/00* (2006.01)
*A61B 17/02* (2006.01)
*A61B 17/29* (2006.01)
*A61F 2/30* (2006.01)

(52) U.S. Cl.
CPC ..... *A61F 2/4611* (2013.01); *A61B 2017/00473* (2013.01); *A61B 2017/00477* (2013.01); *A61B 2017/0256* (2013.01); *A61B 2017/2931* (2013.01); *A61F 2/4603* (2013.01); *A61F 2002/30331* (2013.01); *A61F 2002/30505* (2013.01); *A61F 2002/30522* (2013.01); *A61F 2002/30616* (2013.01); *A61F 2002/4622* (2013.01); *A61F 2002/4628* (2013.01); *A61F 2220/0025* (2013.01); *A61F 2220/0033* (2013.01)
USPC .......................................................... 606/90

(58) Field of Classification Search
USPC .............. 606/90, 205, 52, 208, 207; 600/564; 81/418, 421, 423
See application file for complete search history.

(56) References Cited

U.S. PATENT DOCUMENTS

| 569,839 A | 10/1896 | Roeloffs | |
|---|---|---|---|
| 1,048,937 A * | 12/1912 | Brightwell | 81/415 |
| 1,991,494 A * | 2/1935 | Dempsey | 407/89 |
| 2,606,471 A * | 8/1952 | Kollweck | 81/415 |
| 3,132,550 A * | 5/1964 | Sion | 81/423 |
| 3,840,014 A | 10/1974 | Ling et al. | |
| 3,916,907 A | 11/1975 | Peterson | |
| 4,499,798 A * | 2/1985 | Miskiewicz | 81/423 |
| 4,898,161 A | 2/1990 | Grundei | |
| 4,997,432 A | 3/1991 | Keller | |
| 5,079,977 A * | 1/1992 | Petrie | 81/423 |
| 5,122,130 A | 6/1992 | Keller | |
| 5,297,538 A * | 3/1994 | Daniel | 600/206 |
| 5,387,215 A | 2/1995 | Fisher | |
| 5,430,941 A * | 7/1995 | Lin | 30/260 |
| 5,431,658 A | 7/1995 | Moskovich | |

(Continued)

Primary Examiner — Kathleen Holwerda
Assistant Examiner — Sarah Simpson
(74) Attorney, Agent, or Firm — Nutter McClennen & Fish LLP (57) ABSTRACT

Modular medical instruments and kits are provided, having, a tool body portion with a first mating element at one end. A removable and replaceable modular end effector having a second mating element is matable with the first mating element. The instrument further includes a selectively engageable locking mechanism having a lever arm with a first portion associated with the body portion and a claw portion matingly engageable with a portion of the second mating element of the end effector, the locking mechanism being effective to secure the end effector to the body portion of the modular medical instrument. The invention can be particularly useful for providing a secure connection between the modular end effector and the body portion, yet provide ease of interchangeability between modular end effectors.

13 Claims, 8 Drawing Sheets

(56) References Cited

U.S. PATENT DOCUMENTS

| | | | | |
|---|---|---|---|---|
| 5,443,514 A | | 8/1995 | Steffee | |
| 5,484,437 A | | 1/1996 | Michelson | |
| 5,540,693 A | | 7/1996 | Fisher | |
| 5,540,696 A | | 7/1996 | Booth | |
| 5,554,191 A | | 9/1996 | Lahille | |
| 5,599,279 A | | 2/1997 | Slotman | |
| 5,664,274 A | * | 9/1997 | Collins | 7/129 |
| 5,697,889 A | | 12/1997 | Slotman | |
| 5,716,415 A | | 2/1998 | Steffee | |
| 5,893,875 A | * | 4/1999 | O'Connor et al. | 606/205 |
| 5,899,908 A | | 5/1999 | Kuslich | |
| 5,993,385 A | | 11/1999 | Johnston | |
| 6,017,342 A | | 1/2000 | Rinner | |
| 6,042,542 A | * | 3/2000 | Koros et al. | 600/231 |
| 6,063,088 A | | 5/2000 | Winslow | |
| 6,080,155 A | | 6/2000 | Michelson | |
| 6,083,228 A | | 7/2000 | Michelson | |
| 6,108,845 A | * | 8/2000 | Hung et al. | 7/128 |
| 6,139,508 A | * | 10/2000 | Simpson et al. | 600/564 |
| 6,159,214 A | | 12/2000 | Michelson | |
| 6,233,769 B1 | * | 5/2001 | Seber et al. | 7/128 |
| 6,241,729 B1 | | 6/2001 | Estes | |
| 6,261,296 B1 | | 7/2001 | Aebi | |
| 6,273,882 B1 | * | 8/2001 | Whittier et al. | 606/1 |
| 6,277,122 B1 | | 8/2001 | McGahan | |
| 6,290,724 B1 | | 9/2001 | Marino | |
| 6,332,887 B1 | | 12/2001 | Knox | |
| 6,368,325 B1 | | 4/2002 | McKinley | |
| 6,440,139 B2 | | 8/2002 | Michelson | |
| 6,551,316 B1 | * | 4/2003 | Rinner et al. | 606/57 |
| 6,647,835 B1 | * | 11/2003 | Tseng | 81/423 |
| 6,652,533 B2 | | 11/2003 | O'Neil | |
| 6,663,638 B2 | | 12/2003 | Ralph | |
| 6,709,438 B2 | | 3/2004 | Dixon | |
| 6,712,825 B2 | * | 3/2004 | Aebi et al. | 606/90 |
| 6,716,218 B2 | | 4/2004 | Holmes | |
| 6,721,983 B2 | * | 4/2004 | Dallas et al. | 7/128 |
| 6,739,068 B1 | * | 5/2004 | Rinner | 33/783 |
| 6,764,491 B2 | | 7/2004 | Frey | |
| 7,081,118 B2 | * | 7/2006 | Weber et al. | 606/90 |
| 7,431,723 B2 | * | 10/2008 | Hazebrouck | 606/99 |
| 2001/0029377 A1 | | 10/2001 | Aebi | |
| 2002/0055745 A1 | | 5/2002 | McKinley | |
| 2002/0193802 A1 | * | 12/2002 | Zdeblick et al. | 606/96 |
| 2003/0019110 A1 | * | 1/2003 | Knoop | 30/337 |
| 2004/0039397 A1 | * | 2/2004 | Weber et al. | 606/90 |
| 2005/0010213 A1 | * | 1/2005 | Stad et al. | 606/53 |
| 2006/0036261 A1 | * | 2/2006 | McDonnell | 606/99 |
| 2007/0073405 A1 | * | 3/2007 | Verhulst et al. | 623/17.15 |
| 2007/0100347 A1 | * | 5/2007 | Stad et al. | 606/90 |

* cited by examiner

MODULAR MEDICAL TOOL AND CONNECTOR

FIELD OF THE INVENTION

The invention relates generally to medical tools, and in particular to medical tools with modular, interchangeable components.

BACKGROUND OF THE INVENTION

A variety of surgical tools and instruments are used in surgical procedures. Such tools and instruments have many uses, including use as devices to implant or install prostheses or other implantable elements. Such instruments are particularly prevalent in spinal and orthopaedic surgery.

Due to wide variations in patient size and condition, there is often a need for tools and instruments of different sizes and shapes, particularly in spinal and orthopaedic surgical procedures. As a result, a given surgical procedure may require several instruments of the same general type, each having different sizes and/or shapes. Although modular tools have been proposed, many of such known devices have drawbacks that can render them less than desirable. For example, some devices are difficult to disassemble and reassemble with another modular element. In other cases, the connection between the tool body and the modular component is not sufficiently strong to permit reliable use without excess play between the components.

Thus, there remains a need for a modular surgical instrument that provides a sufficiently strong and rigid connection between the tool body and interchangeable, modular components.

SUMMARY OF THE INVENTION

The present invention provides a modular medical tool that includes a body portion and one or more replaceable and interchangeable end effectors. The end effectors can have different shapes, sizes, and functionalities. An important feature of the invention is the connector that joins the body and the end effector. This connector facilitates an axially aligned connection of these two components. In addition, it is sufficiently strong to resist failure and to substantially eliminate any toggle, or independent movement of one component with respect to the other.

The modular medical instruments of the present invention can include a body portion having a first mating element at one end thereof and a removable and replaceable end effector having a second mating element matable with the first mating element. In one embodiment, the mating element on the body portion is a female receptacle while the mating element of the end effector is a complementary male member. The instrument further includes a selectively engageable locking mechanism including a lever arm having a first portion associated with the body portion and a claw or engagement portion matingly engageable with a portion of the second mating element of the end effector. The locking mechanism is effective to secure the end effector to the body portion of the modular medical instrument. The body portion can take a variety of forms, including a unitary elongate member or a pair of elongate members connected to one another in a pivoting arrangement.

In one embodiment, the present invention can include a body portion wherein the first mating element has at least two substantially flat engagement surfaces. The mating element of the modular end effector likewise has at least two complementary substantially flat engagement surfaces, such that the mating element of the end effector is selectively matable with the mating element of the body portion by placing the substantially flat engagement surfaces in engagement with each other. Further, the locking mechanism includes a lever arm that is movable between a locked position and an unlocked position, and the lever arm has a distal claw member that is adapted to matingly engage a portion of the mating element of the end effector when the locking mechanism is in the locked position. The locking mechanism is effective to secure the end effector to the body portion of the modular medical instrument in a tight clearance fit to provide a secure connection that substantially prevents any toggle between the body and the end effector.

The present invention also provides a modular medical instrument kit for use in a variety of surgical procedures. The kit includes a body portion having a first mating element at one end thereof, and a plurality of removable and replaceable modular end effectors. Each end effector is selectively matable with the first mating element of the body portion, and a selectively engageable locking mechanism ensures a strong and reliable connection between the two components. The end effectors provided with the kit can be of a variety of different sizes, shapes, and types. In addition, end effectors can be included that provide different functionalities.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
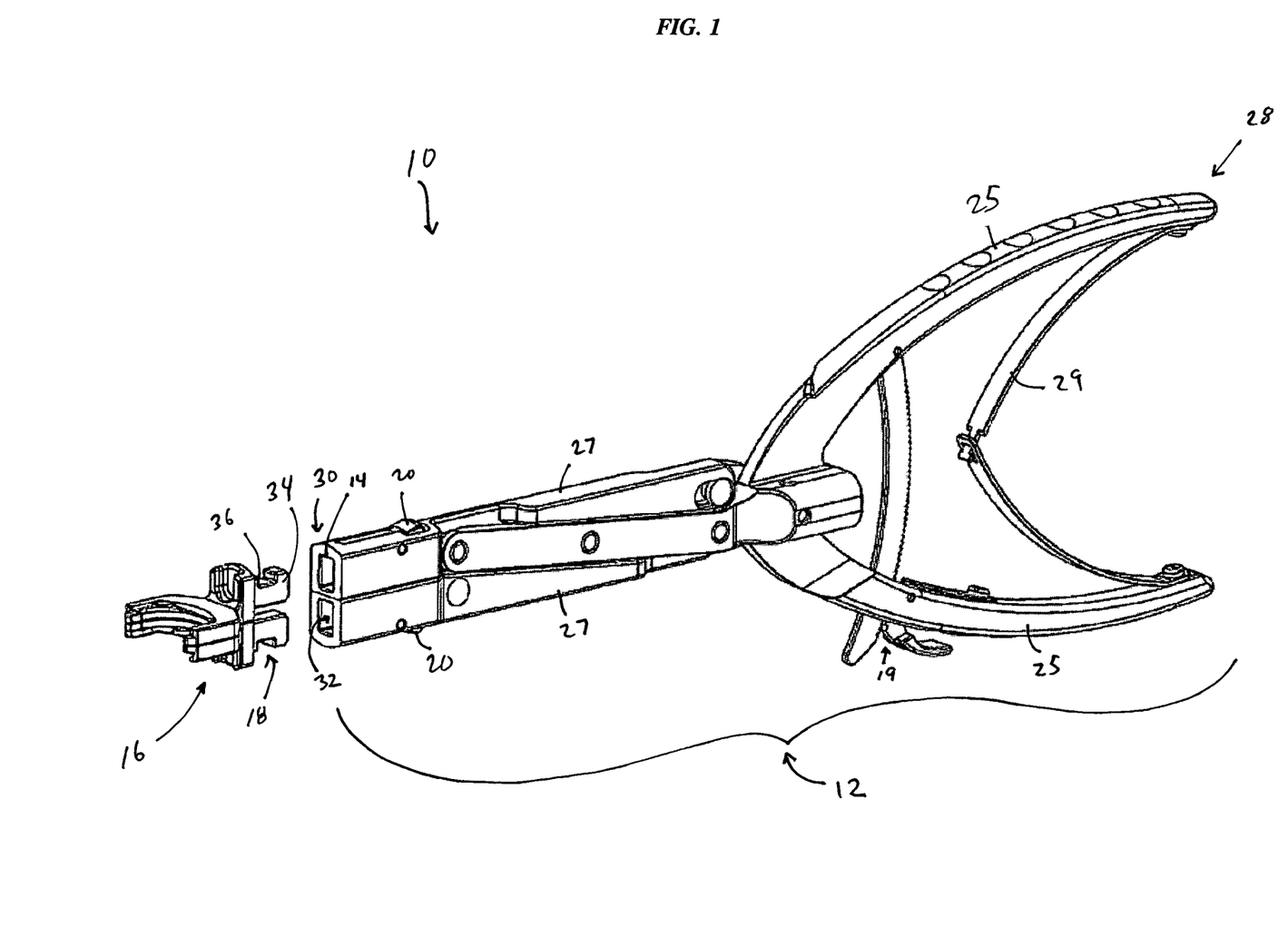
FIG. 1 is a perspective view of an embodiment of the present invention showing a modular medical instrument with interchangeable end effectors uninstalled.

The present invention relates to modular medical instruments and kits that facilitate interchangeability between a medical tool body and various tool tips referred to as end effectors. The end effectors provided with the invention can be of different sizes and shapes, and they can provide different functionality. FIG. 1 illustrates a disassembled view of one embodiment of the modular medical instrument 10 having a body portion 12 with a proximal end 28, a mating element 14 at a distal end 30 thereof and a removable and replaceable modular end effector 16 which has a second mating element 18 matable with the first mating element. The instrument further includes a selectively engageable locking mechanism 20. The locking mechanism 20 is effective to securely connect the end effector 16 to the body portion 12 of the modular medical instrument. In addition, the connection between the components is such that the assembled device can be used in a surgical procedure without failure and with substantially no toggle between the body portion and the end effector.

The devices and kits of the present invention are particularly advantageous in that they allow a surgeon to exchange various modular end effectors efficiently during a surgical procedure without a need to use entirely separate instruments having different sizes or functionalities. Examples of the type of end effectors that can be provided with the present invention include those which provide functionalities including distraction, cutting, retraction, spreading, and insertion.

The modular end effector 16 disclosed herein can be used with a variety of medical instruments that benefit from the tight tolerance fit of the modular tip with a body portion. The invention as disclosed herein is described with reference to insertion forceps, however, one skilled in the art will appreciate that other medical instruments could be substituted such as, for example, modular medical instruments having a single body portion, mating element and end effector as explained in more detail below.

Figure 2:
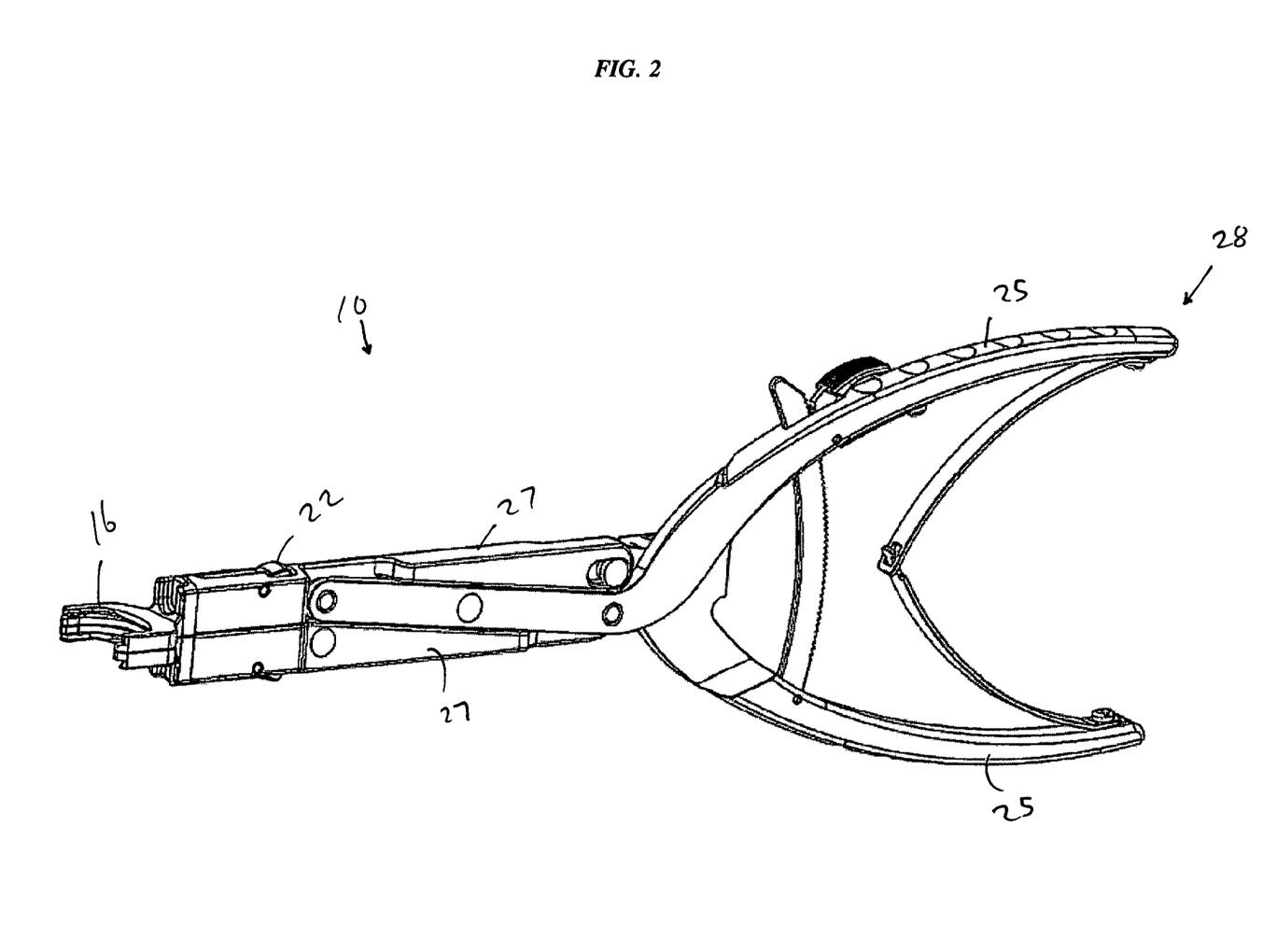
FIG. 2 is a perspective view of an embodiment of the present invention showing a modular medical instrument with interchangeable end effectors installed.
Figure 3:
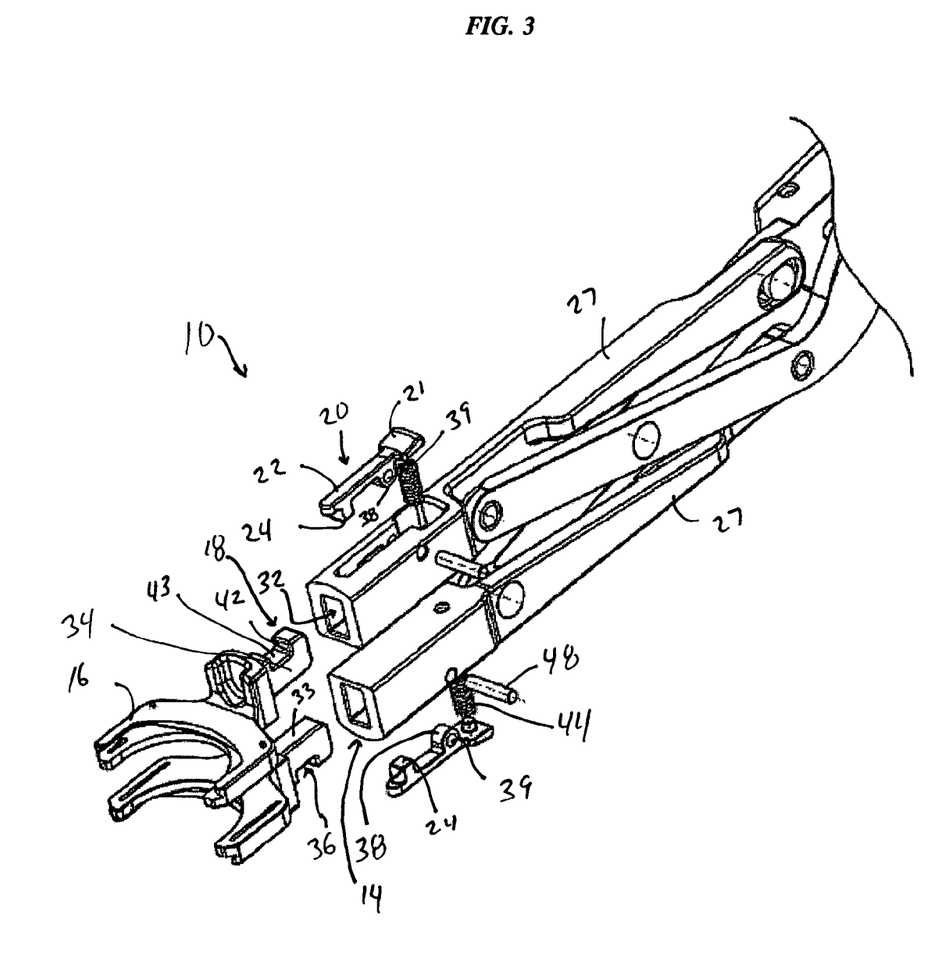
FIG. 3 is a perspective, exploded view of an embodiment of the present invention showing modular end effectors locking mechanisms.

Referring to FIGS. 1-3, one embodiment of the modular medical instrument 10 is an insertion forceps having two elongate members 27, two mating elements 14, and two end effectors 16. The insertion tool can include a body portion 12 having opposed elongate members 27 which can be pivotally connected to one another. The embodiment of FIG. 1 shows a scissors-type connection, however, the elongate members 27 can be pivotally connected to one another by any suitable pivoting connection known to one skilled in the art and is not limited by what is shown. The pivotal connection should also be configured such that movement of the handle portions 25 towards one another effects movement of the elongate members 27, and any attached components, away from one another as shown in FIG. 3. One skilled in the art will appreciate that the handles 25 can be of a variety of shapes and configurations. Moreover, one skilled in the art will appreciate that the instrument can also be configured in an alternative way, in which a movement of the handles towards one another will effect movement of the tips towards one another.

A tool locking mechanism, such as ratchet mechanism 19, can also be provided between the handles 25. The ratchet mechanism 19 allows the elongate members 27 to be releasably locked into position anywhere in the range of movement of the elongate members 27. A handle spring 29 can be positioned between the handles 25 such that when the handle ratchet mechanism 19 is unlocked, the handle spring can return the handles to a "biased-apart" position.

Figure 4:
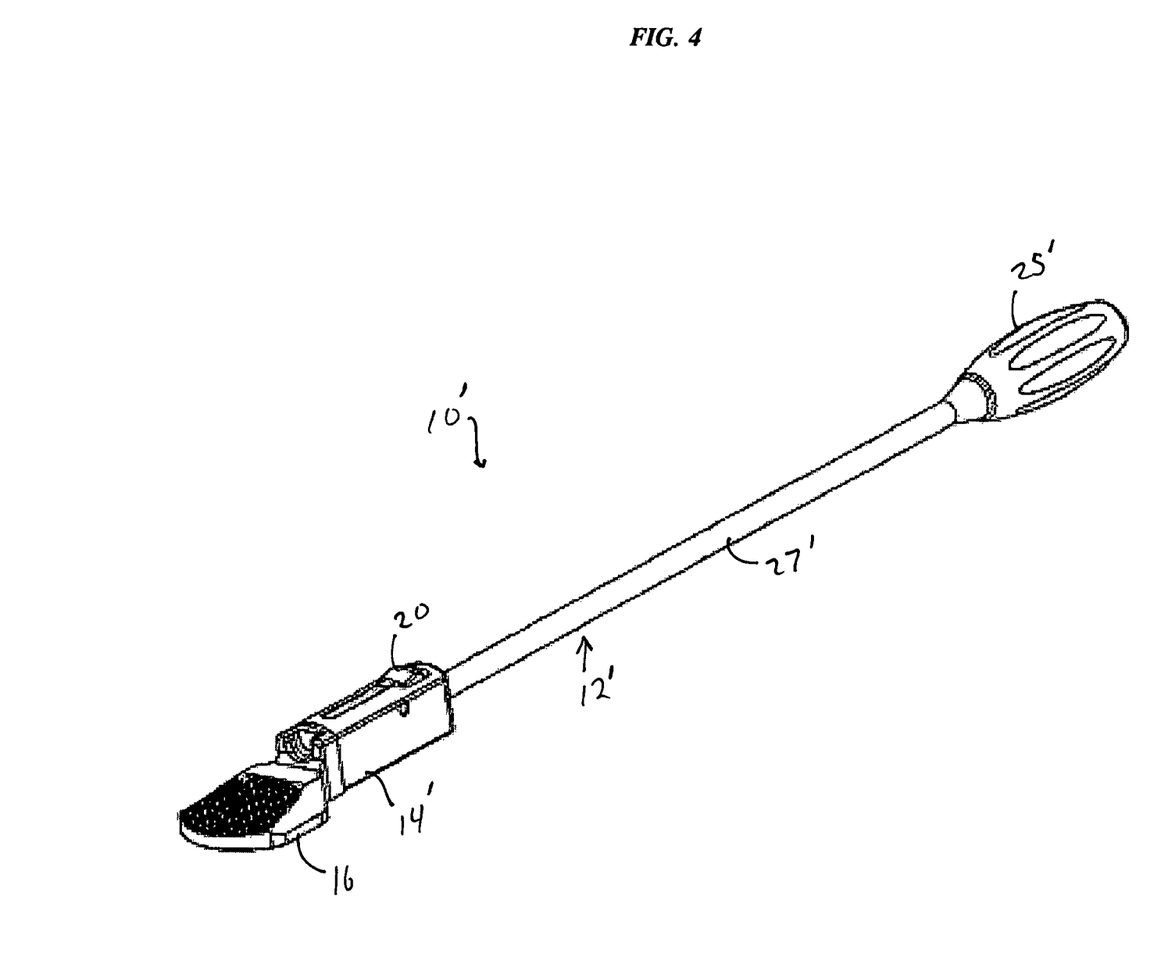
FIG. 4 is a perspective view of another embodiment of the present invention showing a single bodied modular tool with end effector installed.

The body portion 12 can be made of any material such as stainless steel or other material known in the art and suitable for surgical procedures. As further shown in FIG. 1, the elongate members 27 can have a rectangular cross-sectional shape. In addition, the elongate members 27 can be any cross-sectional shape or length, including rectangular (FIG. 1) or circular (FIG. 4). The elongate members 27 should be shaped and sized to facilitate positioning in a body cavity and actuation by a surgeon.

As shown in FIGS. 1 and 3, the first mating element 14 is adapted to receive the second mating element 18 of end effector 16 in a tight clearance fit such that the end effector can be releasably locked into position within the distal end of the elongate member 27. The first mating element 14 can be located on the distal end 30 of the elongate member 27 and is adapted to receive the second mating element 18 (further described below) such that the geometry and dimensions between the first and second mating elements 18 allow for a tight clearance and a complementary fit, as shown in FIG. 2. The tight clearance fit can be in the range of 0.02 mm to 1.0 mm. In one embodiment, as shown in FIG. 1, the first mating element 14 is a female recess 32 that is rectangularly shaped such that it has a height that can be equal to or greater than its width. This orientation allows the mating elements to provide greater strength in the direction of movement (the direction of the scissors action) of the opposed elongate members with respect to one another. However, one skilled in the art will appreciate that the female recess 32 can have many different shapes such as by way of non-limiting example, oval, triangular, circular, and irregular, and that the recess can alternatively be configured as a rectangle having a width that is greater than its height. Further as shown in FIGS. 2 and 3, the female recess 32 can have a depth sufficient to receive the second mating element 18. In the embodiment shown, the female recess 32 has an opening on one surface that is adapted to include a locking mechanism 20 (described below) that is adapted to engage the second mating element and releasably secure it to the elongate member 27.

The second mating element 18, located on the modular end effector 16, is adapted to be correspondingly matable with the first mating element 14 on the elongate member 27. As discussed above with respect to the first mating element 14, the second mating element 18 can also be of any corresponding shape such as by way of non-limiting example, rectangular, oval, triangular, circular, and irregular. In the embodiment shown in FIG. 3, the second mating element 18 is a male member 34 adapted to be received by the female recess 32. FIGS. 1-3 illustrate an embodiment in which the male member 34 is substantially rectangularly shaped such that it has a length sufficient to fully engage the female recess 32 and a height that can be equal to or greater than its width. In another embodiment, the second mating element can be configured as a rectangle with a width that is greater than its height. Further, as shown in FIG. 5, the proximal-facing surface of male member 34 can have a beveled end 35 to provide for easy engagement with the female recess 32.

As further shown in FIG. 3, the male member 34 has a continuous, horizontally-oriented surface 33 and an opposed surface which includes a notch 36 that is adapted to receive the claw portion 24 of locking mechanism 20 such that the locking mechanism can releasably mate the male member with in the female recess 32. In the embodiment shown, the notch 36 has a length and width which are complementary to the dimensions of claw portion 24. It is understood, however, that the notch can have a variety of geometries and dimensions suitable for correspondingly mating with a locking mechanism. The notch 36 can also be open at its sides, as shown in FIG. 3, or can be enclosed on all but one surface that is adapted to receive claw 24. As shown in FIGS. 1 and 3, the notch 36 formed in the male member 34 of the modular end effector 16 can include an undercut in the distal facing surface 42 of the endwall that engages claw 24. The undercut provides a secure lock with the claw portion 24 of the locking mechanism 20 such that it can prevent the male member 34 from unintentionally disengaging from the female recess 32. The undercut in the sidewall should be undercut at an angle in the range of about 1°-45°, and more preferably about 2°-6°, such that surface 42 forms somewhat less than a right angle with a bottom surface 43 of notch 36. In an exemplary embodiment surface 43 is oriented at an angle in the range of about 45°-89°, and more preferably about 84°-88° relative to the bottom surface 43. In another embodiment of the male member 34, shown in FIG. 5, two notches 36 can be located on opposing sides of the male member. Such an embodiment can provide enhanced versatility in that the modular component is able to be mated to the body in different orientations.

Figure 5:
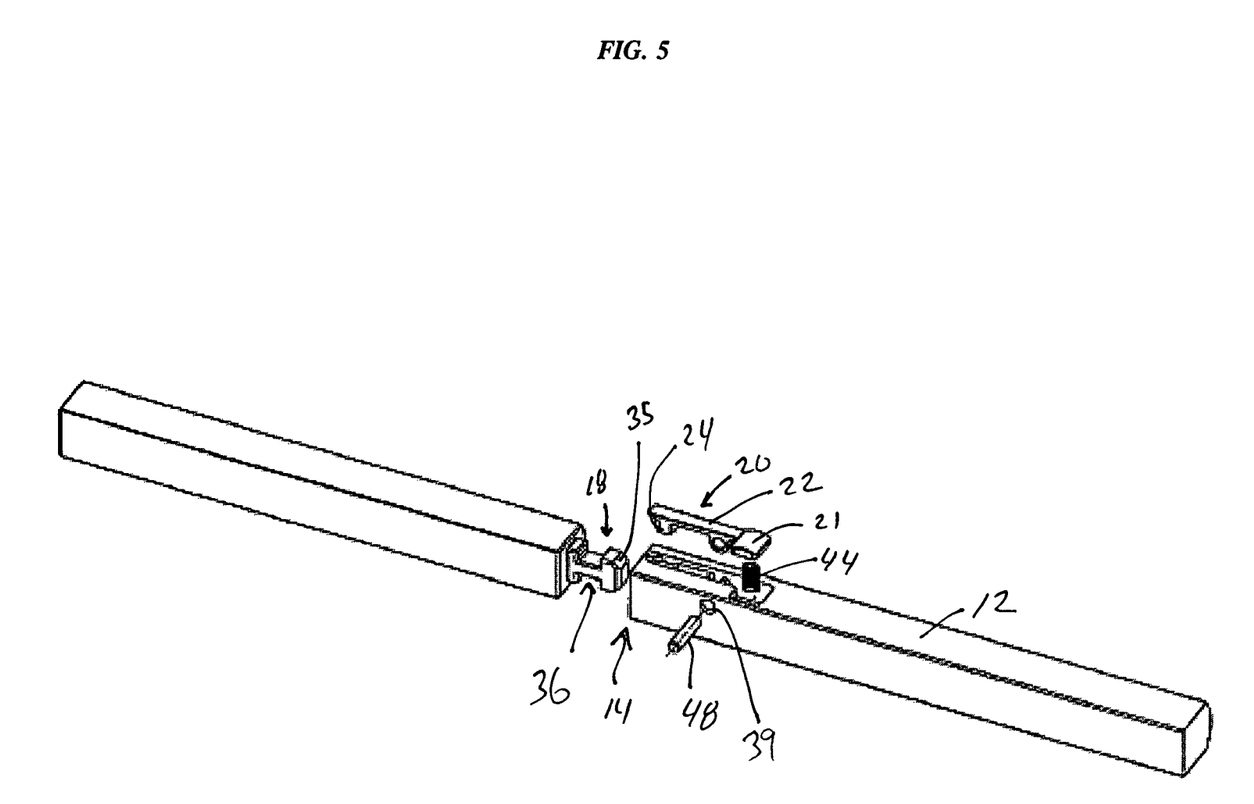
FIG. 5 is a perspective, exploded view of an embodiment of the present invention showing a locking mechanism on a single body portion.
Figure 6:
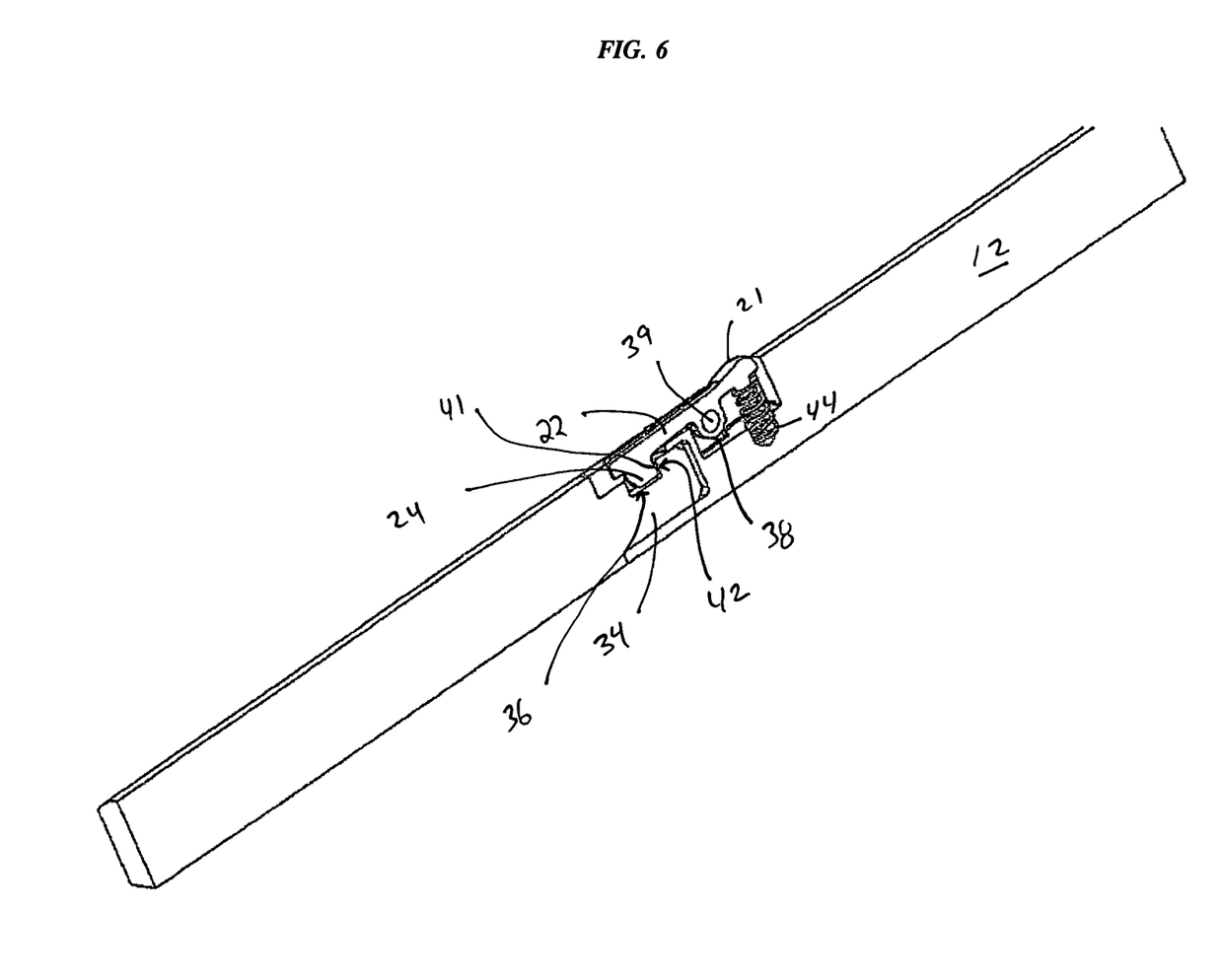
FIG. 6 is a perspective view of an embodiment of the present invention showing a slice of a body portion along the longitudinal axis and a variation of a locking mechanism.

FIGS. 3 and 5, illustrate that first mating element 14 can include an opening in a top portion of elongate element 27 for placement of a locking mechanism 20. As illustrated in FIGS. 3 and 5, the locking mechanism 20 can include a lever arm 22 that is generally elongate with a claw portion 24 at a distal end and an activator button 21 at a proximal end. The lever arm 22 can be pivotally mated to the body portion 12 in a variety of methods known to one skilled in the art. For example, a pin 48 can connect through elongate member 27 and through an aperture 39 formed in fulcrum 38 of the lever arm. The locking mechanism 20 can further include a biasing element 44, such as a spring, shown in FIGS. 3 and 5, that is adapted to bias the lever arm 22 to a locked position. FIG. 6 illustrates the claw portion 24 of locking mechanism 20 in locked engagement with notch 36 of male member 34. As shown, claw 24 is shaped and sized to fit within the notch 36, securing the male member 34 to the first mating element 14. The claw portion 24 may also have an undercut sidewall 41 that is matable with the undercut surface 42 of notch 36. Additional aspects of various locking mechanisms are further described below.

One skilled in the art will appreciate that the relative dimensions of the first and second mating elements can vary depending upon a number of factors, including the geometry of the mating elements and the function of the end effector. In general, the depth of the female recess 32 can be in the range of about 16 mm to 100 mm while the length of the male member 34 can be in the range of about 15 mm to 85 mm. One skilled in the art will appreciate that the relative dimensions can vary and that a variety of alternative designs are possible. By way of example only, in one embodiment, the depth of the female recess 32 is in the range of about 16 mm to 22 mm, while the length of the male member 34 is in the range of about 15 to 21 mm. In another embodiment, for example, the depth of the female recess 32 is in the range of about 90 mm to 100 mm, while the length of the male member 34 is in the range of about 75 mm to 85 mm. In addition, the relative height and width of the female recess and male member should be such that a tight clearance fit can be achieved. Generally, the clearance between female receptacle 32 and male member 34 is in the range of about 0.02 mm to 1.0 mm. Further, the clearance between notch 36 and claw 24 should also provide a secure fit and be in the range of about 0.01 mm to 1.0 mm.

Figure 7:
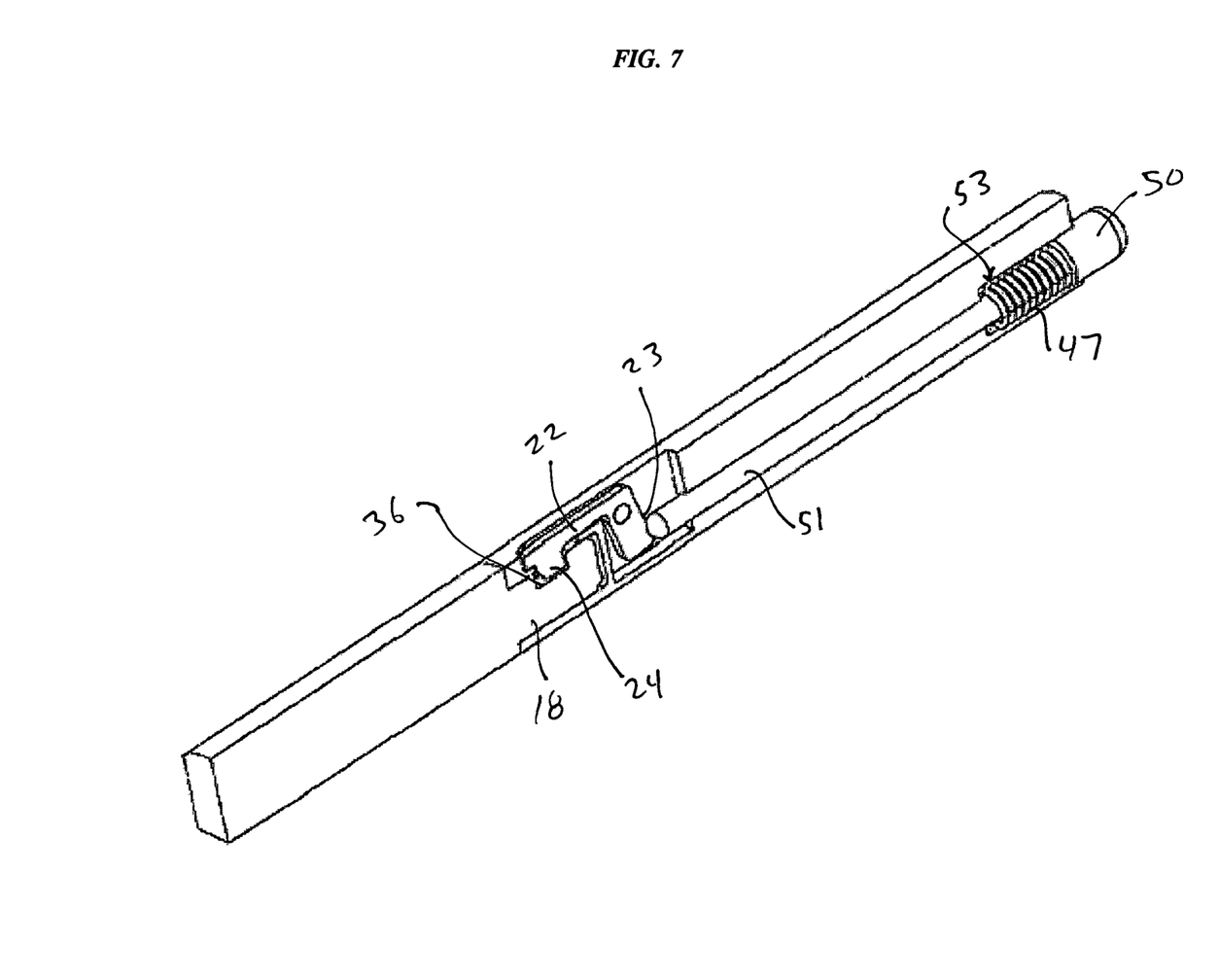
FIG. 7 is a perspective view of another embodiment of the present invention showing a slice of a body portion along the longitudinal axis and another variation of a locking mechanism.

FIG. 7 shows another embodiment of locking mechanism 20 in which the locking mechanism can be activated by a trigger or push button so at a proximal portion of tool body 12. In this embodiment a proximal portion 23 of lever arm 22 communicates with trigger shaft 51 that extends from trigger 50 through the tool body 12. A biasing element 47, seated in a recess 53 of the tool body 12, acts on a distal-facing surface of trigger 50 to bias locking mechanism to the locked position. A force applied to trigger 50 will cause the distal end of shaft 51 to act on the proximal portion 23 of lever arm 22, thus raising claw 24 out of engagement with notch 36.

Figure 8:
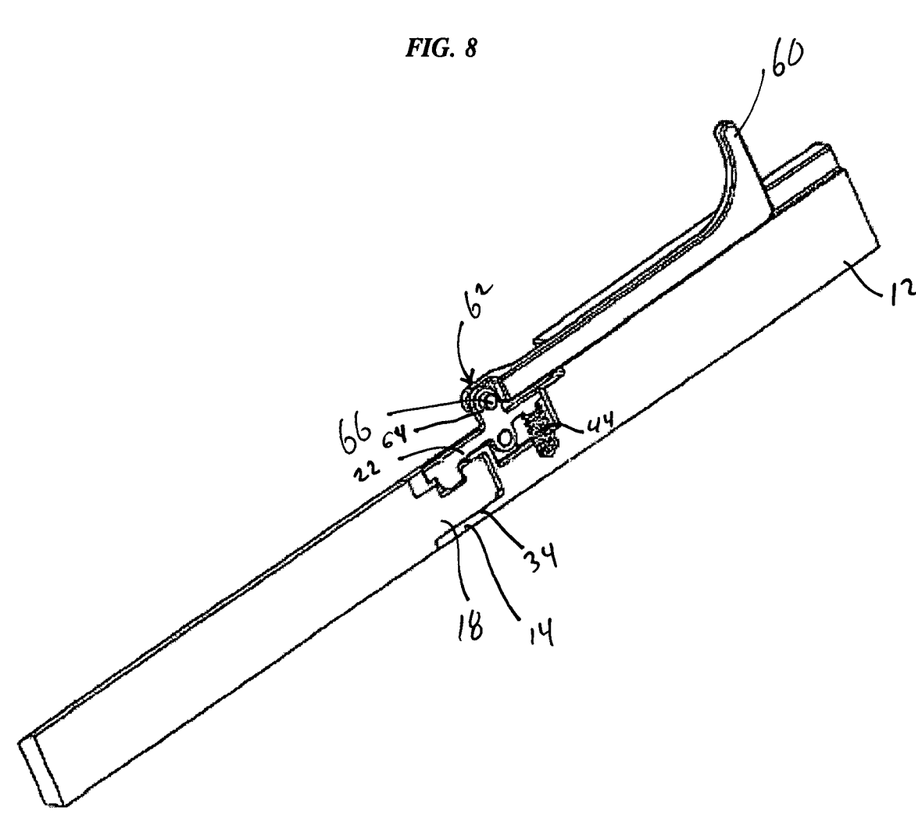
FIG. 8 is a perspective view of yet another embodiment of the present invention showing a slice of a body portion along the longitudinal axis and yet another variation of a locking mechanism.

FIG. 8 shows yet another aspect of a locking mechanism 20 of the present invention. In this aspect, a pull-trigger 60 is positioned at a location near the proximal end 28 of the body portion 12 to activate locking mechanism 20. As illustrated, the locking mechanism is pivotally connected to the tool body 12 in a manner similar to that described above with respect to FIGS. 3 and 5. That is, a pin 48 connects to the lever arm 22 through an aperture 39 formed in fulcrum arm 38 of the lever arm. In addition, the distal end 62 of the trigger shaft connects a second fulcrum 64 on the lever arm 22 through a pivot pin 66. The pull-trigger 60 is adapted such that a proximal movement of the pull-trigger causes the lever arm 22 to pivot such that the claw portion 24 of the lever arm is raised and becomes disengaged from the notch 36 in the male member 34. One skilled in the art will appreciate that the locking mechanism can be actuated from the proximal end of the instrument by variety of other designs.

FIG. 4 illustrates another embodiment of the present invention in which the body portion 12' is a unitary elongate member 27', having a handle portion 25' at a proximal end and a first mating element 14' at a distal end thereof. The first mating element 14 is likewise releasably matable with end effector 16, which has a male mating element similar to that described above with respect to FIGS. 1-3. One skilled in the art will readily appreciate that a variety of end effectors 16, having a variety of shapes, sizes, and functionalities, can be used with the tool of FIG. 4.

The invention has been described herein with the tool body having a female mating element and the end effector having a male mating element. One skilled in the art will readily appreciate, however, that the mating element of the tool body can be male and that the mating element of the end effector can be female.

The present invention also encompasses a modular medical instrument kit that can include one or more end effectors of varying shapes, sizes and functions for use with a single tool body portion. The kit is adapted to allow a surgeon to easily exchange different end effectors with a single tool body during a surgical procedure. An end effector can be easily removed and replaced with a new end effector that best suits the needs of the surgeon. Once an end effector is removed, a new one can be mated to the tool body by simply moving the two components axially towards each other. During the mating process, the claw portion 24 of the locking mechanism 20 engages a notch 36 in the male locking element to ensure a solid and reliable connection between the two components, substantially free of toggle, and to avoid any unintentional disengagement. In order to disassemble an end effector 16 from the body portion 12, the lever arm 22 is actuated to disengage the claw 24 from the notch 16 in the male member 34 and the end effector is moved axially away from the tool body.

In use, the modular medical instrument kit can be used in a variety of surgical procedures depending on the functionality of the end effectors. In one embodiment, the modular medical instrument of the present invention can be effective as an insertion and spreading forceps using end effectors that are effective to separate adjacent vertebral bodies and to insert an implant within the intervertebral space. Such end effectors can be available in a variety of sizes. One skilled in the art will also appreciate that the modular medical instrument of the invention can be modified to perform other functions, e.g., to effect compressive forces.

The end effectors can be of the type that have parallel or oblique spreading tips. Such tips are used for trialing purposes and, as such, they have the same shape, size, thickness and angle as an associated implant endplate. These end effectors are available in a variety of sizes and geometries, for example, as parallel (0°), 5°, 7.5°, and 10°. Such end effectors are also available in the above-mentioned angles for a variety of implant sizes.

The end effectors provided with the kit of the present invention can also be central spreading tips. These tips are offset from the primary axis of the modular medical instrument by 20 degrees. Such tips are available in several footprint sizes, and function to provide adequate distraction of the disc space to allow the surgeon to reach the posterior aspects of the surgical level.

Accordingly, the embodiments of the present invention are not limited by what has been particularly shown and described, except as indicated by the appended claims. All publications and references cited herein are expressly incorporated herein by reference in their entirety.

What is claimed is:

1. A modular medical instrument, comprising:
a body portion having a first mating element at a distal end thereof, the mating element having at least one substantially flat engagement surface;
at least one removable and replaceable modular end effector having a second mating element, the second mating element having at least one complementary substantially flat engagement surface, having first and second notches formed in opposing sides thereof such that the notches form first and second substantially rectangular recesses in the opposing sides of the second mating element such that the second mating element has an I shape and a rectangular cross-sectional shape, and being selectively matable with the first mating element by placing the complementary substantially flat engagement surface in engagement with the substantially flat engagement surface of the first mating element; and
a selectively engageable locking mechanism including a lever arm movable between a locked position and an unlocked position, the lever arm having a protruding distal claw member that is configured to selectively and matingly engage within the first notch of the second mating element of the end effector when the locking mechanism is in the locked position, the locking mechanism being effective to secure the end effector to the body portion of the modular medical instrument when the end effector is continuously axially moved toward the locking mechanism from outside the body portion;
wherein the lever arm of the locking mechanism is coupled to a trigger at a proximal portion of the instrument by a trigger shaft extending through the body portion of the instrument such that actuating the trigger causes movement of the lever arm.

2. The instrument of claim 1, wherein the first and second mating elements and the locking mechanism permit a connection between the body portion and the end effector with substantially no relative movement between the body portion and the end effector.

3. The instrument of claim 1, wherein the first mating element is a female receptacle formed in a distal end of the body portion.

4. The instrument of claim 3, wherein the second mating element is a male member formed on a proximal end of the end effector.

5. The instrument of claim 3, wherein the female receptacle has a substantially rectangular cross section.

6. The instrument of claim 5, wherein the female receptacle has a depth in the range of about 16 mm to 100 mm.

7. The instrument of claim 5, wherein the female receptacle has a height that is greater than its width.

8. The instrument of claim 5, wherein the female receptacle has a height that is substantially equal to its width.

9. The instrument of claim 1, wherein the body portion comprises a unitary element.

10. The instrument of claim 1, wherein the body portion comprises opposed first and second elongate members pivotally connected to one another.

11. The instrument of claim 10, wherein there are at least two end effectors and the first mating element is formed on a proximal end of each of the first and second elongate members and matable with one of the at least two end effectors.

12. A modular medical instrument kit, comprising:
a body portion having a first mating element at a distal end thereof;
a plurality of removable and replaceable modular end effectors, each having a second mating element being selectively matable with the first mating element, and at least one of the plurality of end effectors having a different function than at least one other of the plurality of end effectors; and
a selectively engageable locking mechanism including a lever arm movable between a locked position and an unlocked position, the lever arm having a protruding distal claw member that is configured to matingly engage within a recess formed in the second mating element of one of the end effectors when the locking mechanism is in the locked position such that an undercut distal-facing surface of the second mating element mates with an undercut proximal-facing surface of the distal claw member such that the distal-facing surface of the second mating element forms less than a right angle with a bottom surface of the recess formed in the second mating element, and such that a perimeter of the first mating element surrounds a perimeter of the second mating element in a tight clearance fit and there is less than one millimeter of misalignment relative to one another around the perimeters of the first and second mating elements, the locking mechanism being effective to secure the end effector to the body portion of the modular medical instrument;
wherein the lever arm of the locking mechanism is coupled to a trigger at a proximal portion of the instrument by a trigger shaft extending through the body portion of the instrument such that actuating the trigger causes movement of the lever arm.

13. The instrument kit of claim 12, wherein at least one of the second mating elements has a second recess formed on an opposing side of the recess formed in the at least one of the second mating elements, the at least one of the second mating elements being selectively matable with the first mating element such that when the locking mechanism is in the locked position, only a selected one of the two recesses of the at least one second mating element mates with the undercut proximal-facing surface of the protruding distal claw member.

* * * * *